United States Patent
Walsh et al.

(12) 
(10) Patent No.: US 6,288,078 B1
(45) Date of Patent: Sep. 11, 2001

(54) 6-AZAINDOLE COMPOUNDS AS ANTAGONISTS OF GONADOTROPIN RELEASING HORMONE

(75) Inventors: Thomas F. Walsh, Watchung; Feroze Ujjainwalla, Edison, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/520,331

(22) Filed: Mar. 7, 2000

Related U.S. Application Data

(60) Provisional application No. 60/123,616, filed on Mar. 10, 1999.

(51) Int. Cl.[7] .................. C07D 471/04; C07D 221/02; A61K 31/495
(52) U.S. Cl. ............... 514/300; 546/113; 546/117; 546/118; 514/303
(58) Field of Search .................. 546/113, 117, 546/118; 514/300, 303

(56) References Cited

U.S. PATENT DOCUMENTS

| | | | |
|---|---|---|---|
| 4,544,663 | 10/1985 | Manning et al. | 514/378 |
| 5,030,640 | 7/1991 | Fisher et al. | 514/339 |
| 5,756,507 | 5/1998 | Goulet et al. | 514/19 |
| 5,780,437 | 7/1998 | Goulet et al. | 514/226.8 |
| 5,849,764 | 12/1998 | Goulet et al. | 514/337 |

FOREIGN PATENT DOCUMENTS

| | | |
|---|---|---|
| 879 381 | 2/1980 | (BE) . |
| 679 642 | 11/1995 | (EP) . |
| 2 181 559 | 12/1973 | (FR) . |
| WO 90/05721 | 5/1990 | (WO) . |
| WO 95/29900 | 11/1995 | (WO) . |
| WO 97/21703 | 6/1997 | (WO) . |
| WO 97/21707 | 6/1997 | (WO) . |

OTHER PUBLICATIONS

Ortmann and Diedrich, Pituitary and extrapituitary actions of gonadotrophin–releasing hormone and its analogues, Human Reproduction, 14: 194–206, Jan. 1999.*

Annu. Rev. Med., vol. 45, pp. 391–405 (1994), by Conn, et al.

Drugs of the Future, vol. 13, No. 8. pp. 761–787 (1988), by A. S. Dutta.

Current Opinion in Obstetrics & Gynocology, vol. 6, pp. 262–268 (1994), by R. A. Loy.

TEM, vol. 3, No. 1, pp. 30–34 (1992), by R. L. Barbieri.

Drugs, vol. 35, pp. 63–82 (1988), by Filicori, et al.

Human Reproduction, vol. 11, Suppl. 1 (1996), by G. Hodgen.

Human Reproduction, vol. 11, Suppl. 3 (1996), by U. Cirkel.

J. Med. Chem., vol. 32, pp. 2036–2038 (1989), by Clark, et al.

J. of the Chemical Society, pp. 459–463 (1970), by Herbert, et al.

* cited by examiner

*Primary Examiner*—Richard L. Raymond
*Assistant Examiner*—Hong Liu
(74) *Attorney, Agent, or Firm*—Soonhee Jang; Mark R. Daniel

(57) ABSTRACT

There are disclosed compounds of formula (I)

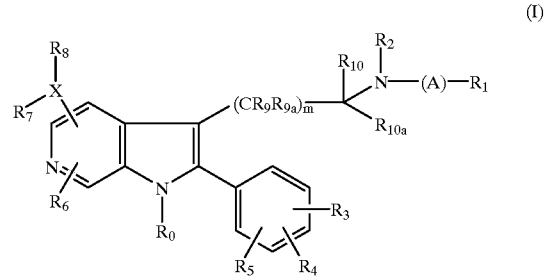

(I)

and pharmaceutically acceptable salts thereof which are useful as antagonists of GnRH and as such may be useful for the treatment of a variety of sex-hormone related and other conditions in both men and women.

18 Claims, No Drawings

6-AZAINDOLE COMPOUNDS AS ANTAGONISTS OF GONADOTROPIN RELEASING HORMONE

This application claims the benefit of U.S. Provisional Application No. 60/123,616, filed Mar. 10, 1999.

BACKGROUND OF THE INVENTION

The gonadotropin-releasing hormone (GnRH), also referred to as luteinizing hormone-releasing hormone (LHRH), is a decapeptide that plays a key role in human reproduction. The hormone is released from the hypothalamus and acts on the pituitary gland to stimulate the biosynthesis and secretion of luteinizing hormone (LH) and follicle-stimulating hormone (FSH). LH released from the pituitary gland is primarily responsible for the regulation of gonadal steroid production in both sexes, whereas FSH regulates spermatogenesis in males and follicular development in females. GnRH agonists and antagonists have proven effective in the treatment of certain conditions which require inhibition of LH/FSH release. In particular, GnRH-based therapies have proven effective in the treatment of endometriosis, uterine fibroids, poly-cystic ovarian disease, precocious puberty and several gonadal steroid-dependent neoplasia, most notably cancers of the prostate, breast and ovary. GnRH agonists and antagonists have also been utilized in various assisted fertilization techniques and have been investigated as a potential contraceptive in both men and women. They have also shown possible utility in the treatment of pituitary gonadotrophe adenomas, sleep disorders such as sleep apnea, irritable bowel syndrome, premenstrual syndrome, benign prostatic hyperplasia, hirsutism, as an adjunct to growth hormone therapy in growth hormone deficient children, and in murine models of lupus. The compounds of the invention may also be used in combination with bisphosphonates (bisphosphonic acids) and other agents, such as growth hormone secretagogues, for the treatment and the prevention of disturbances of calcium, phosphate and bone metabolism, in particular, for the prevention of bone loss during therapy with the GnRH antagonist, and in combination with estrogens, progesterones, antiestrogens, antiprogestins and/or androgens for the prevention or treatment of bone loss or hypogonadal symptoms such as hot flashes during therapy with the GnRH antagonist.

Additionally, a compound of the present invention may be co-administered with a 5a-reductase 2 inhibitor, such as finasteride or epristeride; a 5a-reductase 1 inhibitor such as 4,7b-dimethyl-4-aza-5a-cholestan-3-one, 3-oxo-4-aza-4,7b-dimethyl-16b-(4-chlorophenoxy)-5a-androstane, and 3-oxo-4-aza-4,7b-dimethyl-16b-(phenoxy)-5a-androstane as disclosed in WO 93/23420 and WO 95/11254; dual inhibitors of 5a-reductase 1 and 5a-reductase 2 such as 3-oxo-4-aza-17b-(2,5-trifluoro-methylphenyl-carbamoyl)-5a-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Further, a compound of the present invention may be used in combination or co-administered with a compound having luteinizing hormone releasing activity such as a peptide or natural hormone or analog thereof. Such peptide compounds include leuprorelin, gonadorelin, buserelin, triptorelin, goserelin, nafarelin, histrelin, deslorelin, meterlin and recirelin.

Additionally, a compound of the present invention may be used as described in U.S. Pat. No. 5,824,286 which discloses the administration of peptide GnRH antagonists such as Antide and azaline B to premenopausal women to enhance the readability of mammographic film relative to a mammogram effected in the absence of the administration.

Current GnRH antagonists are GnRH-like decapeptides which are generally administered intravenously or subcutaneously presumably because of negligible oral activity. These have amino acid substitutions usually at positions one, two, three, six and ten.

Non-peptide GnRH antagonists offer the possible advantage of oral adminstration. Non-peptide GnRH antagonists have been described in European Application 0 219 292 and in De, B. et al., J. Med. Chem., 32, 2036–2038 (1989), in WO 95/28405, WO 95/29900 and EP 0679642 all to Takeda Chemical Industries, Ltd.

Substituted indoles known in the art include those described in the following patents and patent applications. U.S. Pat. No. 5,030,640 discloses alpha-heterocyclic ethanol aminoalkyl indoles which are potent β-agonists. U.S. Pat. No. 4,544,663 discloses indolamine derivatives which are allegedly useful as male anti-fertility agents. WO 90/05721 discloses alpha-amino-indole-3-acetic acids useful as anti-diabetic, anti-obesity and anti-atherosclerotic agents. French patent 2,181,559 discloses indole derivatives with sedative, neuroleptic, analgesic, hypotensive, antiserotonin and adrenolytic activity. Belgian patent 879381 discloses 3-aminoalkyl-1H-indole-5-thioamide and carboxamide derivatives as cardiovascular agents used to treat hypertension, Raynaud's disease and migraine. U.S. Pat. Nos. 5,756,507, 5,780,437 and 5,849,764 also disclose substituted arylindoles as non-peptide antagonists of GnRH.

SUMMARY OF THE INVENTION

The present invention relates to compounds which are non-peptide antagonists of GnRH which can be used to treat a variety of sex-hormone related conditions in men and women, to methods for their preparation, and to methods and pharmaceutical compositions containing said compounds for use in mammals.

Because of their activity as antagonists of the hormone GnRH, the compounds of the present invention are useful to treat a variety of sex-hormone related conditions in both men and women. These conditions include endometriosis, uterine fibroids, polycystic ovarian disease, hirsutism, precocious puberty, gonadal steroid-dependent neoplasias such as cancers of the prostate, breast and ovary, gonadotrophe pituitary adenomas, sleep apnea, irritable bowel syndrome, premenstrual syndrome and benign prostatic hypertophy. They are also useful as an adjunct to treatment of growth hormone deficiency and short stature, and for the treatment of systemic lupus erythematosis. Further, the compounds of the invention may be useful in in vitro fertilization and as contraceptives. The compounds may also be useful in combination with androgens, estrogens, progesterones, antiestrogens and antiprogestogens for the treatment of endometriosis, fibroids and in contraception. They may also be useful in combination with testosterone or other androgens or antiprogestogens in men as a contraceptive. The compounds may also be used in combination with an angiotensin-converting enzyme inhibitor such as Enalapril or Captopril, an angiotensin II-receptor antagonist such as Losartan or a renin inhibitor for the treatment of uterine fibroids. Additionally, the compounds of the invention may also be used in combination with bisphosphonates (bisphosphonic acids) and other agents, for the treatment and the prevention of disturbances of calcium, phosphate and bone metabolism, in particular, for the prevention of bone loss during therapy with the GnRH antagonist, and in combination with estrogens, progesterones and/or androgens for the prevention or treatment of bone loss or hypogonadal symptoms such as hot flashes during therapy with the GnRH antagonist.

Additionally, a compound of the present invention may be co-administered with a 5a-reductase 2 inhibitor, such as finasteride or episteride; a 5a-reductase 1 inhibitor such as 4,7b-dimethyl-4-aza-5a-cholestan-3-one, 3-oxo-4-aza-4,7b-dimethyl-16b-(4-chlorophenoxy)-5a-androstane, and 3-oxo-4-aza-4,7b-dimethyl-16b-(phenoxy)-5a-androstane as disclosed in WO 93/23420 and WO 95/11254; dual inhibitors of 5a-reductase 1 and 5a-reductase 2 such as 3-oxo-4-aza-17b-(2,5-trifluoro-methylphenyl-carbamoyl)-5a-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Further, a compound of the present invention may be used in combination or co-administered with a compound having luteinizing hormone releasing activity such as a peptide or natural hormone or analog thereof. Such peptide compounds include leuprorelin, gonadorelin, buserelin, triptorelin, goserelin, nafarelin, histrelin, deslorelin, meterlin and recirelin.

Additionally, a compound of the present invention may be used as described in U.S. Pat. No. 5,824,286 which discloses the administration of peptide GnRH antagonists such as Antide and azaline B to premenopausal women to enhance the readability of mammographic film relative to a mammogram effected in the absence of the administration.

DETAILED DESCRIPTION OF THE INVENTION

The present invention relates to compounds of the general formula

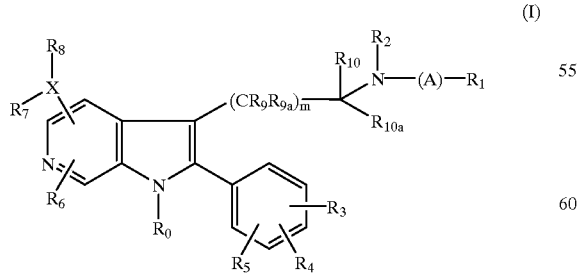

(I)

wherein

A is $C_1$–$C_6$ alkyl, substituted $C_1$–$C_6$ alkyl, $C_3$–$C_7$ cycloalkyl, substituted $C_3$–$C_7$ cycloalkyl, $C_3$–$C_6$ alkenyl, substituted $C_3$–$C_6$ alkenyl, $C_3$–$C_6$ alkynyl, substituted $C_3$–$C_6$ alkynyl, $C_1$–$C_6$ alkoxy, or $C_0$–$C_5$ alkyl-S(O)$_n$—$C_0$–$C_5$ alkyl, $C_0$–$C_5$ alkyl-O—$C_0$–$C_5$ alkyl, $C_0$–$C_5$ alkyl-NR$_{18}$—$C_0$–$C_5$ alkyl where $R_{18}$ and the $C_0$–$C_5$ alkyl can be joined to form a ring, or a single bond.

$R_0$ is hydrogen, $C_1$–$C_6$ alkyl, substituted $C_1$–$C_6$ alkyl, wherein the substituents are as defined below; aryl, substituted aryl, aralkyl or substituted aralkyl, wherein the substituents are as defined for $R_3$, $R_4$ and $R_5$.

$R_1$ is

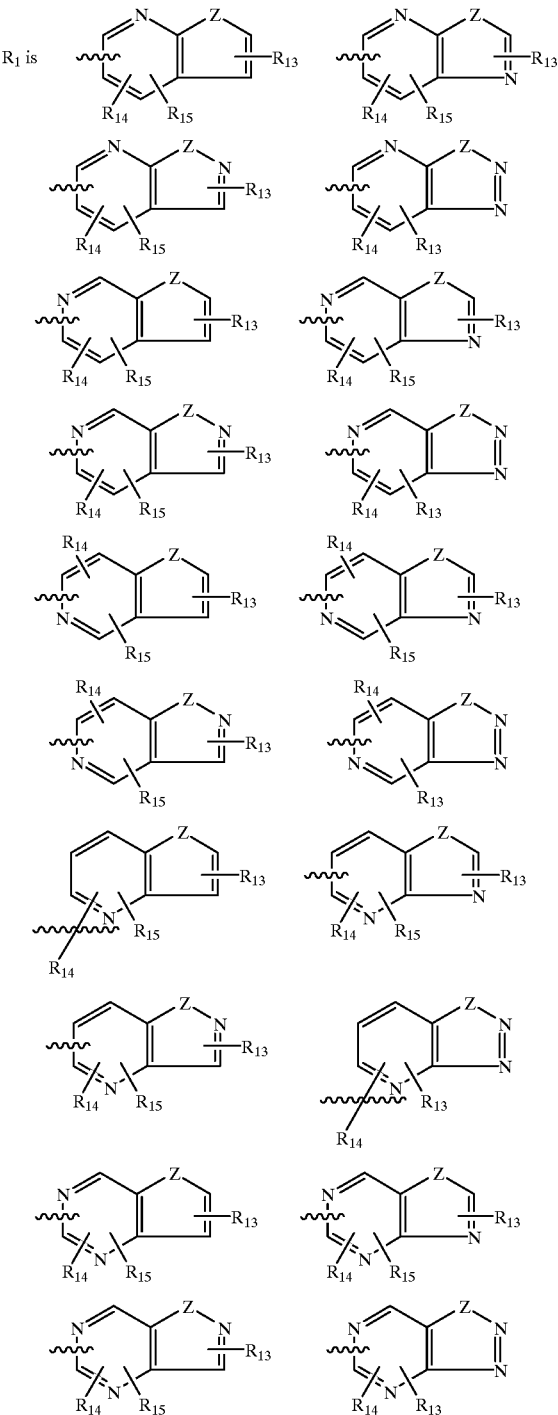

-continued

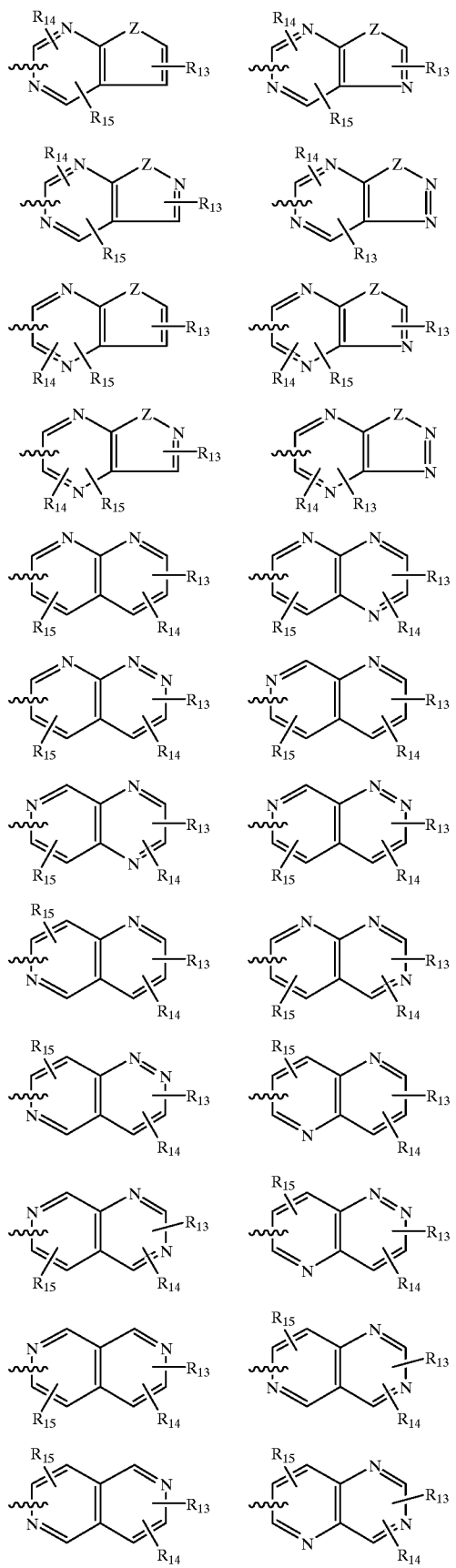
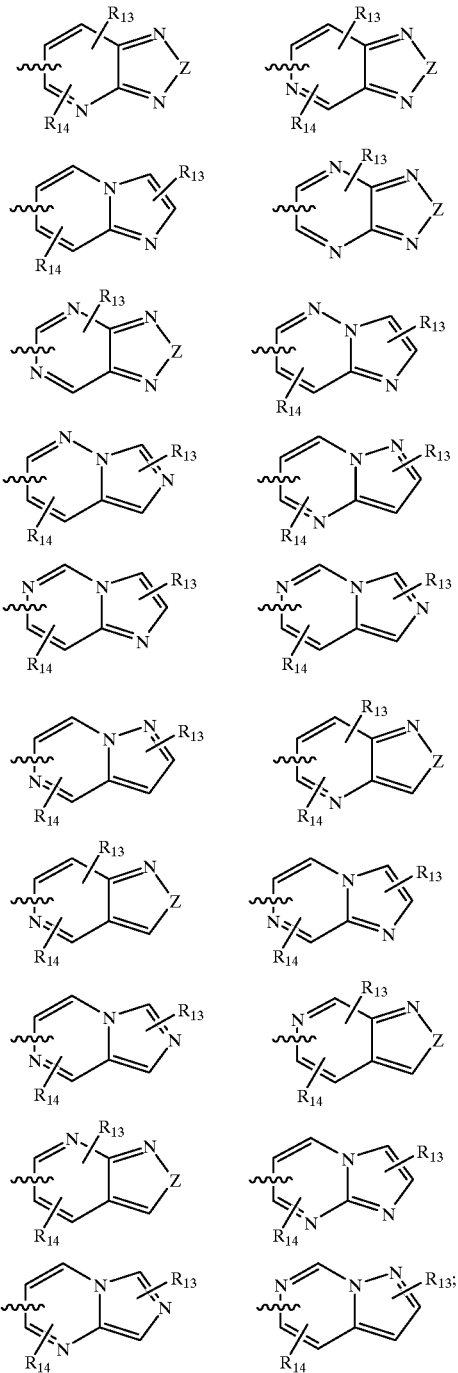

the nitrogen atoms contained in the $R_1$ heteroaromatic rings may exist either as drawn or, when chemically allowed, in their oxidized (N→O) state;

$R_2$ is hydrogen, $C_1$–$C_6$ alkyl, substituted $C_1$–$C_6$ alkyl, aralkyl, substituted aralkyl, aryl, substituted aryl, alkyl—$OR_{11}$, $C_1$–$C_6(NR_{11}R_{12})$, $C_1$–$C_6(CONR_{11}R_{12})$ or $C(NR_{11}R_{12})NH$;

$R_2$ and A taken together form a ring of 5–7 atoms;

$R_3$, $R_4$ and $R^5$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_3$ and $R_4$ taken together form a carbocyclic ring of 3–7 carbon atoms or a heterocyclic ring containing 1–3 heteroatoms selected from N, O and S;

$R_6$ is hydrogen, $C_1$–$C_6$ alkyl, substituted $C_1$–$C_6$ alkyl, aryl, substituted aryl, $C_1$–$C_3$ perfluoroalkyl, CN, $NO_2$, halogen, $R_{11}O(CH_2)_p$—, $NR_{12}C(O)R_{11}$, $NR_{12}C(O)NR_{11}R_{12}$ or $SO_nR_{11}$;

R7 is hydrogen, $C_1$–$C_6$ alkyl, or substituted $C_1$–$C_6$ alkyl, unless X is hydrogen or halogen, then $R_7$ is absent;

$R_8$ is hydrogen, $C(O)OR_9$, $C(O)NR_{11}R_{12}$, $NR_{11}R_{12}$, $C(O)R_{11}$, $NR_{12}C(O)R_{11}$, $NR_{12}C(O)NR_{11}R_{12}$, $NR_{12}S(O)_2R_{11}$, $NR_{12}S(O)_2NR_{11}R_{12}$, $OC(O)R_{11}$, $OC(O)NR_{11}R_{12}$, $OR_{11}$, $SO_nR_{11}$, $S(O)_nNR_{11}R_{12}$, $C_1$–$C_6$ alkyl or substituted $C_1$–$C_6$ alkyl, unless X is hydrogen or halogen, then $R_8$ is absent; or $R_7$ and $R_8$ taken together form a carbocyclic ring of 3–7 atoms;

$R_9$ and $R_{9a}$ are independently hydrogen, $C_1$–$C_6$ alkyl, substituted $C_1$–$C_6$ alkyl; aryl or substituted aryl, aralkyl or substituted aralkyl when m≠0; or $R_9$ and $R_{9a}$ taken together form a carbocyclic ring of 3–7 atoms or $$\overset{O}{\underset{\|}{}}$$

when m≠0;

$R_9$ and A taken together form a heterocyclic ring containing 3–7 carbon atoms and one or more heteroatoms when m≠0; or $R_{10}$ and $R_{10a}$ are independently hydrogen, $C_1$–$C_6$ alkyl, substituted $C_1$–$C_6$ alkyl, aryl, substituted aryl, aralkyl or substituted aralkyl; or $R_{10}$ and $R_{10a}$ taken together form a carbocyclic ring of 3–7 atoms or $$\overset{O}{\underset{\|}{}};$$

$R_9$ and $R_{10}$ taken together form a carbocyclic ring of 3–7 carbon atoms or a heterocyclic ring containing one or more heteroatoms when m≠0; or $R_9$ and $R_2$ taken together form a heterocyclic ring containing 3–7 carbon atoms and one or more heteroatoms when m≠0; or $R_{10}$ and $R_2$ taken together form a heterocyclic ring containing 3–7 carbon atoms and one or more heteroatoms;

$R_{10}$ and A taken together form a heterocyclic ring containing 3–7 carbon atoms and one or more heteroatoms; or $R_{11}$ and $R_{12}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

$R_{11}$ and $R_{12}$ taken together can form an optionally substituted ring of 3–7 atoms;

$R_{13}$ is hydrogen, OH, $NR_7R_8$, $NR_{11}SO_2(C_1$–$C_6$ alkyl), $NR_{11}SO_2$(substituted $C_1$–$C_6$ alkyl), $NR_{11}SO_2$(aryl), $NR_{11}SO_2$(substituted aryl), $NR_{11}SO_2(C_1$–$C_3$ perfluoroalkyl); $SO_2NR_{11}(C_1$–$C_6$ alkyl), $SO_2NR_{11}$(substituted $C_1$–$C_6$ alkyl), $SO_2NR_{11}$(aryl), $SO_2NR_{11}$(substituted aryl), $SO_2NR_{11}(C_1$–$C_3$ perfluoroalkyl); $SO_2NR_{11}(C(O)C_1$–$C_6$ alkyl); $SO_2NR_{11}(C(O)$-substituted $C_1$–$C_6$ alkyl); $SO_2NR_{11}(C(O)$-aryl); $SO_2NR_{11}(C(O)$-substituted aryl); $S(O)_n(C_1$–$C_6$ alkyl); $S(O)_n$(substituted $C_1$–$C_6$ alkyl), $S(O)_n$(aryl), $S(O)_n$(substituted aryl), $C_1$–$C_3$ perfluoroalkyl, $C_1$–$C_3$ perfluoroalkoxy, $C_1$–$C_6$ alkoxy, substituted $C_1$–$C_6$ alkoxy, COOH, halogen, $NO_2$ or CN;

$R_{14}$ and $R_{15}$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_{18}$ is hydrogen, $C_1$–$C_6$ alkyl, substituted $C_1$–$C_6$ alkyl, $C(O)OR_9$, $C(O)NR_{11}R_{12}$, $C(O)R_{11}$, $S(O)_nR_{11}$;

$R_{19}$ is either the definition of $R_{13}$ or $R_{14}$;

X is hydrogen, halogen, N, O, $S(O)_n$, $C(O)$, $(CR_{11}R_{12})_p$; $C_2$–$C_6$ alkenyl, substituted $C_2$–$C_6$ alkenyl, $C_2$–$C_6$ alkynyl, or substituted $C_2$–$C_6$ alkynyl; when X is hydrogen or halogen, $R_7$ and $R_8$ are absent; when X is O, $S(O)_n$, $C(O)$, or $CR_{11}R_{12}$ only $R_7$ or $R_8$ is possible;

Z is O, S, or $NR_{11}$;

m is 0–3;

n is 0–2;

p is 0–4; and the alkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, $C(O)OR_{11}$, aryl $C_1$–$C_3$ alkoxy, substituted aryl $C_1$–$C_3$ alkoxy, and the aryl substituents are as defined for $R_3$, $R_4$ and $R_5$;

or a pharmaceutically acceptable addition salt and/or hydrate thereof, or where applicable, a geometric or optical isomer or racemic mixture thereof.

Unless otherwise stated or indicated, the following definitions shall apply throughout the specification and claims.

When any variable (e.g., aryl, heterocycle, $R_1$, etc.) occurs more than one time in any constituent or in formula I, its definition on each occurrence is independent of its definition at every other occurrence. Also, combinations of substituents and/or variables are permissible only if such combinations result in stable compounds.

The term "alkyl" is intended to include both branched and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), secbutyl (s-Bu), tertbutyl (t-Bu), isopentane, isohexane, etc.

The term "aryl" includes phenyl and naphthyl. In a preferred embodiment, aryl is phenyl.

The term "halogen" or "halo" is intended to include fluorine, chlorine, bromine and iodine.

As used herein, the term "composition" is intended to encompass a product comprising the specified ingredients in the specified amounts, as well as any product which results, directly or indirectly, from combination of the specified ingredients in the specified amounts It is intended that the connecting group A can be bonded to any of the available carbon or heteroatoms of the heteroaromatic groups $R_1$, including both rings of the benzo-fused heterocyclic groups and, likewise, $R_{13}$, $R_{14}$, and $R_{15}$ can be bonded to any of the available carbon atoms of the heteroaromatic groups $R_1$.

In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers or diasteromers, e.g., racemates, as well as individual enantiomers or diastereomers of the instant compound are included. These individual enantiomers are commonly designated according to the optical rotation they effect by the symbols (+) and (−), (L) and (D), (1) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical fomula or name shall encompass pharmaceuticaly acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts Examples of acid salts are hydrochloric, nitric, sulfuric, phosphoric, formic, acetic, trifluoroacetic, propionic, maleic, succinic, malonic, methanesulfonic, benzenesulfonic and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl) aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis characteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The compounds of the invention are prepared according to the following reaction schemes. All of the substituents are as defined above unless indicated otherwise.

Reaction Scheme A

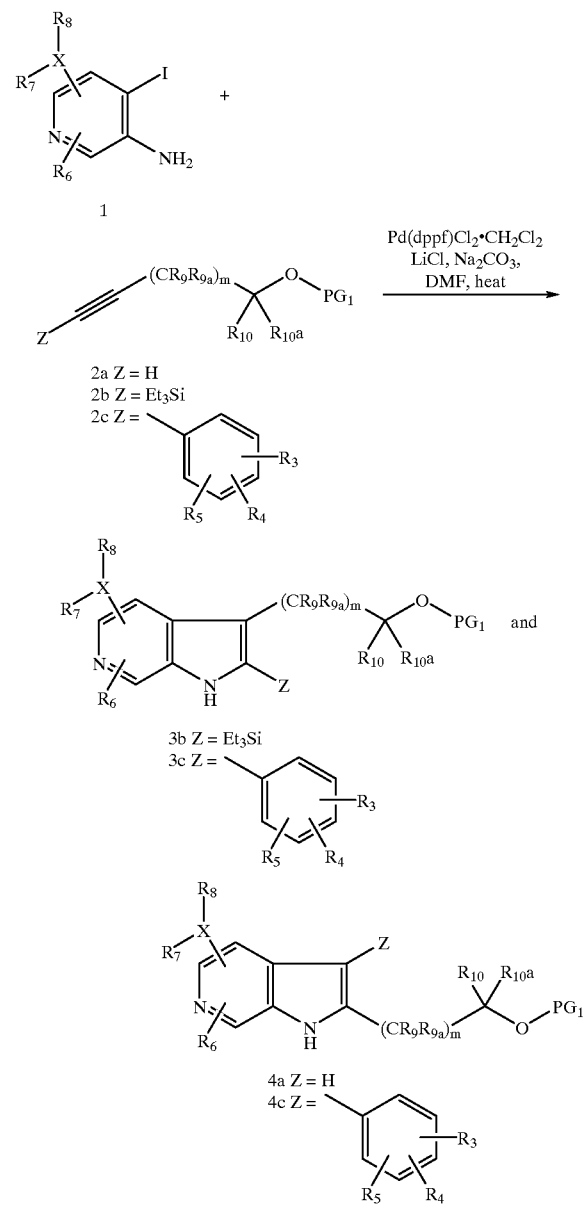

A preferred method for the synthesis of the substituted tryptamines described in this invention utilizes a palladium-catalyzed cross coupling reaction as a key step as shown in Scheme A. This 6-azaindole synthesis involves the reaction of a suitably functionalized 3-amino-4-iodopyridine (1) with substituted acetylenes such as 2 in the presence of a base like sodium carbonate, lithium chloride, and a palladium catalyst such as (dppf)PdCl$_2$•CH$_2$Cl$_2$. The reaction is conducted in an inert organic solvent such as dimethylformamide at elevated temperatures, for instance at 100° C., and the reaction is conducted for a period of about 30 minutes to about 24 hours. A standard workup and isolation affords the substituted isomeric indole derivatives 3 and 4, and the isomer of general formula 3 is the preferred isomer. The acetylene utilized in this reaction may be a terminal acetylene (2a) or be optionally substituted on the terminal carbon atom with a substituent Z (2b, 2c). The substituent abbreviated PG$_1$ indicates an alcohol protecting group such as a benzyl ether, tert-butyl ether or the like. The nature of the Z substituent determines the distribution of the 6-azaindole isomers (3 and 4) produced in the reaction. For example, if the substituent Z on the acetylene is a hydrogen atom then the isomer 4a is the major product of the reaction. When the substituent Z is chosen to be a substituted silyl group such as trimethylsilyl, triethylsilyl (as shown), or the like, then isomer 3b is formed almost exclusively. When Z is a substituted aryl group, then both isomers 3c and 4c may be formed and the product mixture is separated using chromatographic or crystallization techniques to afford the individual isomers.

If the synthesis is conducted with a silyl-substituted acetylene 2b to produce a silyl-substituted 6-azaindole 3b, then the silyl group is next converted to an aryl or substituted aryl group of general formula 3c using the reactions described later in Scheme E. The 2-arylsubstituted 6-azaindole derivatives 3c formed either directly from arylacetylenes (2c) as shown in Scheme A or from 2-trialkylsilyl-6-azaindoles using the method of Scheme E are then further elaborated as described below to produce the novel 6-azaindole derivatives described in this invention.

Reaction Scheme B

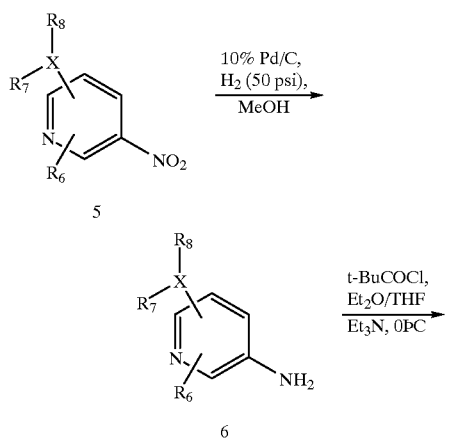

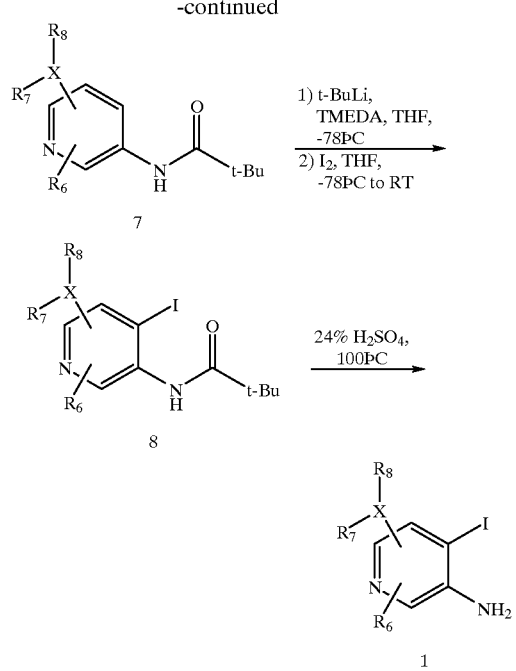

Scheme B illustrates the preparation of substituted 3-amino-4-iodopyridines (1) which are utilized in the 6-azaindole synthesis described in Scheme A. Substituted 3-nitropyridine derivatives such as 5 are useful starting materials for the preparation of 3-amino-4-iodopyridines (1). The 3-nitropyridines (5) bearing the desired substituents can in turn be prepared by the nitration of a pyridine derivative, by a nucleophilic aromatic substitution reaction from a suitable halogenated nitropyridine or by other methods known in the chemical literature. The nitro substituent of a 3-nitropyridine is readily reduced to the required 3-amino group using a variety of methods such as catalytic hydrogenation and the resulting 3-amino group can then serve as a directing group for the subsequent introduction of an iodine at the 4 position of the pyridine. To facilitate the introduction of the iodine atom the 3-amino group is first converted to a good ortho-directing substituent such as a pivalamide (7). This is achieved by reacting the 3-aminopyridine 6 with pivaloyl chloride in the presence of an amine base like triethylamine in a suitable inert solvent followed by a standard workup and isolation. The resulting pivalamide 7 is then subjected to ortho-lithiation by treatment with a strong organolithium base such as tert-butyl lithium in the presence of a N,N,N',N'-tetramethylethylene diamine. The ortho-lithiation is conducted in an inert solvent such as tetrahydrofuran at low temperature, typically −78° C., and the 4-lithiated derivative is the predominant regioisomer formed. Once the lithiation reaction is complete the reaction mixture is then treated with an iodinating reagent like iodine or iodine monochloride in a compatable solvent such as tetrahydrofuran and then allowed to warm to room temperature. Workup and product purification affords the 4-iodopyridine derivative 8 which in the final step is converted to the substituted 3-amino-4-iodopyridines of general formula 1 by removal of the ortho-directing group. In the case illustrated in reaction Scheme B where a pivaloyl group was chosen as the ortho-directing group it may be removed by hydrolysis under acidic conditions such as treatment with sulfuric acid at an elevated temperature.

Reaction Scheme C

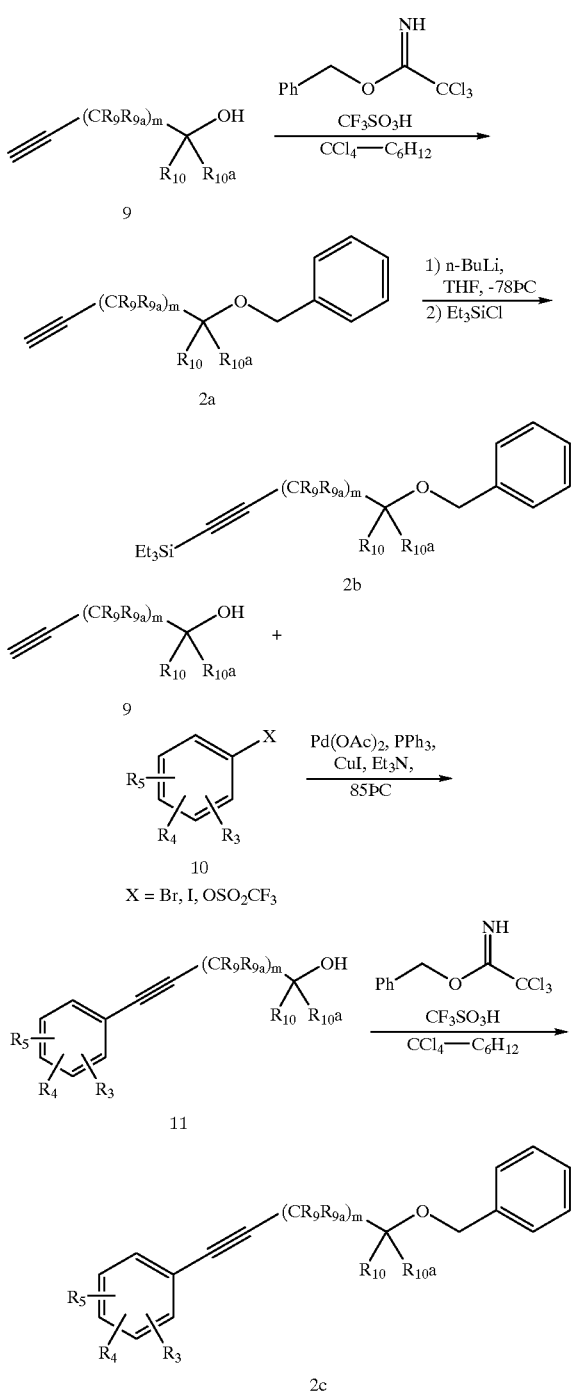

O-benzyl ether. Thus, reaction of 10 with O-benzyl-2,2,2-trichloroacetimidate in the presence of a catalytic amount of a strong acid such as trifluoromethanesulfonic acid and in a suitable inert organic solvent like carbon tetrachloride at room temperature affords after 2 to 24 hours the protected acetylenic alcohol 2a. Compounds of formula 2a may in turn be converted to acetylenes (2b) of general formula 2 wherein Z is a trialkylsilyl group by deprotonation of the acetylene with a base such as n-butyllithium in an inert organic solvent like tetrahydrofuran followed by reaction with a trialkylsilyl chloride such as triethylchlorosilane. The deprotonation and silylation reactions are generally conducted at low temperatures, for instance between about $-78°$ C. and room temperature, and after standard workup and purification a silylacetylene of formula 2b is obtained.

As previously stated, acetylenes of general formula 2c wherein Z is an aryl or substituted aryl group, are also useful in the 6-azaindole synthesis illustrated in Scheme A. Arylacetylenes 2c may be prepared using a coupling reaction of cuprous acetylides derived from acetylenic alcohols of formula 2a with various aryl halides or aryl triflates (11). Such coupling reactions produce aryl acetylenes of general formula 12 as shown at the bottom of Scheme C. These reactions are generally carried out in a basic organic solvent like triethylamine at elevated temperatures, typically between about $60°$ C. and about $120°$ C., and the coupling reaction is catalyzed by copper(I) salts such as cuprous iodide and a palladium catalyst such as palladium acetate in combination with triphenylphosphine. The hydroxyl group of the arylacetylenes of general formula 12 can be protected with a suitable protecting group such as the O-benzyl ether group shown in Scheme C, to afford an arylacetylene (2c) of general formula 2 wherein Z is an aryl or substituted aryl group. It is also recognized that in some cases it may be preferable to reverse the order of the steps illustrated in Scheme C. For instance, acetylenic alcohols (7) may be subjected to silylation or arylation prior to the hydroxyl group protection step.

Reaction Scheme D

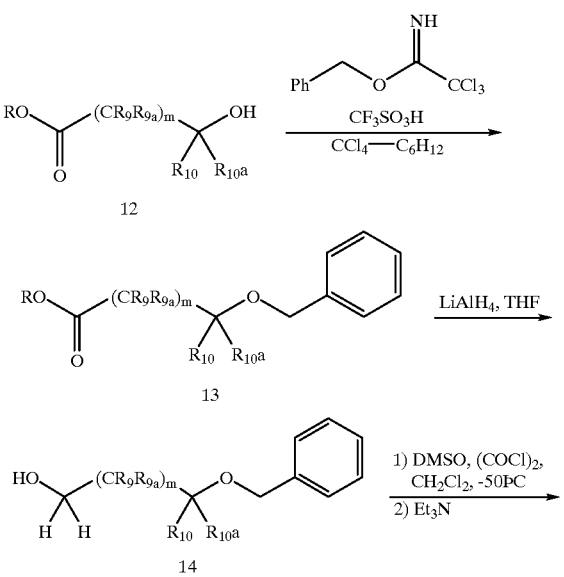

Acetylenic compounds of general structure 2 are prepared using one of several methods depending upon the choice of the desired substituents. When the substituents $R_9$, $R_{9a}$, $R_{10}$ and $R_{10a}$ are selected to be hydrogen or lower alkyl groups, compounds of formula 2 may be prepared from known acetylenic alcohols such as 3-butyn-1-ol, 4-pentyn-2-ol or similar acetylenic alcohols reported in the chemical literature. The conversion of acetylenic alcohols of general formula 10 to acetylene derivatives of general formula 2 is shown in Scheme C. For clarity the hydroxyl protecting group ($PG_1$) illustrated in Scheme C is exemplified as an

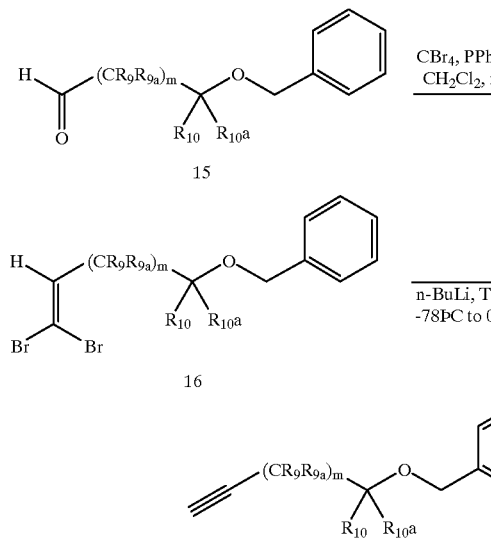

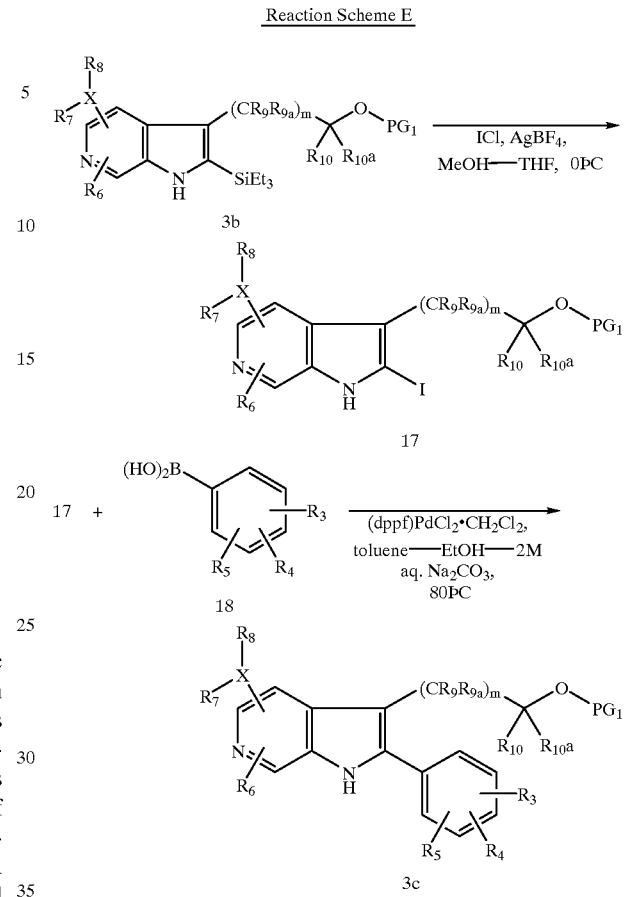

Reaction Scheme E

Another useful approach for the preparation of acetylenic compounds of general formula 2a employs an ethynylation reaction sequence of aldehydes of general formula 16 as shown in Scheme D. The aldehydes (16) used in the ethynylation sequence may be prepared using various methods known in organic synthesis starting with hydroxy-esters of general formula 13, from protected hydroxyesters of formula 14, or from alcohols related to the mono-hydroxyl protected diols of formula 15. The choice of preferred starting material depends upon the nature of the substituents $R_9$, $R_{9a}$, $R_{10}$, and $R_{10a}$ selected. Scheme D illustrates this strategy begining with the generalized hydroxy ester 13. Protection of the hydroxyl group of 13, for instance as the O-benzylether shown, affords a protected hydroxy ester of formula 14. The ester group of compounds of formula 14 can then be converted to an aldehyde of formula 16 either directly using a reagent like diisobutylaluminum hydride in a solvent like toluene, or through a two step process. In the two step process, reduction of the ester group with a reagent such as lithium aluminum hydride in tetrahydrofuran affords alcohols of formula 15 which are then subjected to reoxidation, for instance using a Swern-Moffatt oxidation, to afford the desired aldehydes of formula 16.

The ethynylation of aldehydes of formula 16 is accomplished in two steps. First, aldehydes (16) are reacted with carbon tetrabromide and triphenylphosphine in an inert organic solvent like dichloromethane to produce the dibromo olefins of formula 17. Next, the dibromo olefins (17) are treated with two equivalents of a strong base such as n-butyllithium in tetrahydrofuran at low temperature, for instance at about −78° C. The strong base induces dehydrohalogenation and metal-halogen exchange to afford lithium acetylides which upon quenching and workup afford acetylenes of general formula 2a. Alternatively, the intermediate lithium acetylides formed in the reaction may be treated with a trialkylsilyl chloride, such as triethylchlorosilane, to afford silylacetylenes of general formula 2b.

The conversion of 2-silyl-substituted 6-azaindoles of general formula 3b to 2-aryl-substituted 6-azaindoles of general formula 3c may be accomplished in two steps as shown in Scheme E. The first step is a halodesilylation reaction which converts silyl-substituted 6-azaindoles of formula 3b into 2-halo-6-azaindoles of general formula 18. Scheme E illustrates this process using iodine monochloride so that the product obtained is a 2-iodoindole of general formula 18. Silver tetrafluoroborate is also employed in this example to increase the reactivity of the halogenating reagent. It is possible to effect the halodesilylation reaction with other electrophilic halogenating reagents such as N-bromosuccinimide in dichloromethane which affords a 2-bromo-6-azaindole derivative. Both 2-bromo and 2-iodo-6-azaindoles of formula 18 are useful in the subsequent step.

The second step is a palladium-catalyzed cross coupling reaction of the 2-halo-6-azaindole 18 with a suitable aryl or substituted aryl organometallic reagent 19. Scheme E illustrates this process with an aryl or substituted arylboronic acid as the organometallic reagent, however, other organometallic reagents known to participate in palladium-catalyzed cross-coupling reactions such as arylboronic esters or arylstannanes may also be employed. In the example, a 2-iodo-6-azaindole of general formula 18 is coupled with a generalized boronic acid (19) using a catalyst such as [1,1'-bis(diphenylphosphino)ferrocene] dichloropalladium(II) complex with dichloromethane (shown), tetrakis (triphenylphosphine)-palladium(0) or the like. The reaction is usually conducted at temperatures between room temperature and about 100° C., for instance at about 80° C. This palladium catalyzed cross-coupling reaction may be effected using various combinations of palladium catalysts and solvent compositions known in organic chemistry, and the selection of the conditions is made depending upon the type of organometallic reagent (19) used and the identity of the substituent groups in the two starting materials. When the organometallic reagent is a boronic acid or boronate ester then a preferred solvent mixture consists of toluene, ethanol and an aqueous solution of a base like cesium or sodium carbonate. If instead the organometallic reagent 19 is an arylstannane, then no additional base is required, and a polar aprotic solvent such as tetrahydrofuran or dimethylformamide is employed.

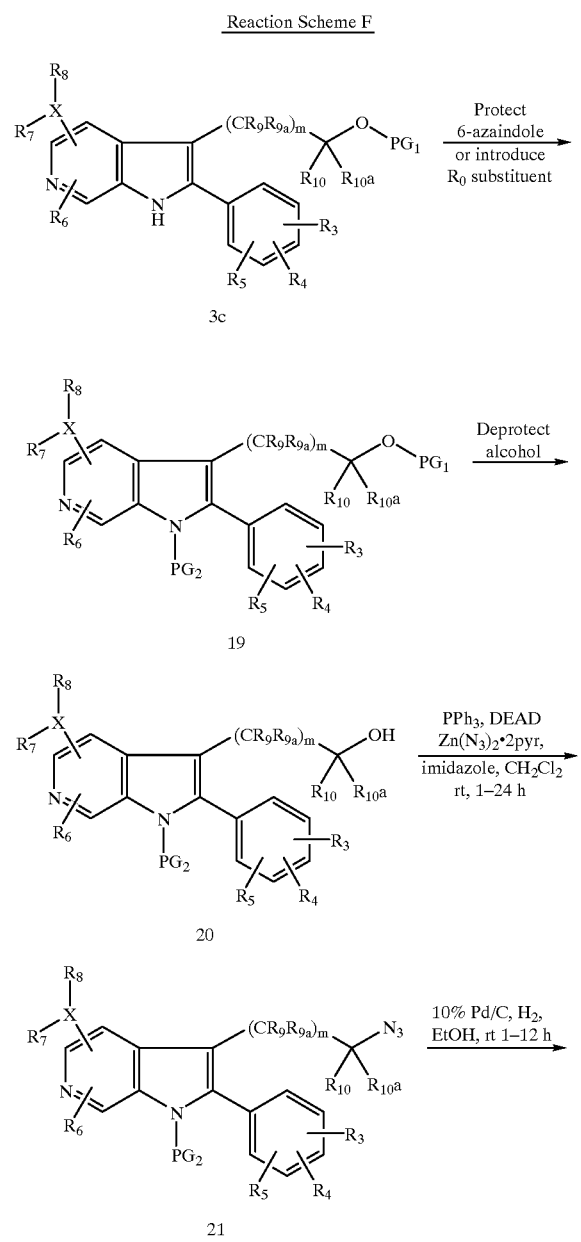

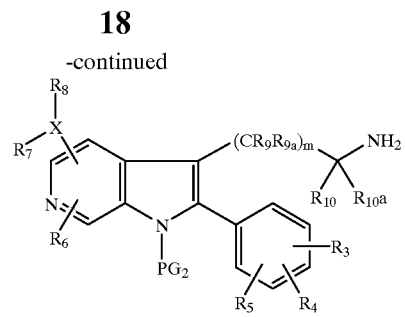

22

The next stage of the synthesis of the novel 6-azaindole derivatives is illustrated in Scheme F. This sequence of reactions begins with protection of the 6-azaindole with an amine protecting group ($PG_2$) to afford compounds of general formula 20. The protection step is required to avoid competing side rections of the 2-aryltryptophol of formula 21 (where $PG_2$ is H) in the later conversion of compounds of formula 21 to compounds of formula 22. The indole protection is followed by removal of the hydroxyl protecting group ($PG_1$) from the side chain at the C-3 position of the 6-azaindole ring to afford compounds of general formula 21. Finally, the hydroxyl group of 21 is converted to a primary amine of general formula 23 which is then further functionalized as shown below in the following schemes. The choice of an appropriate amine protecting group ($PG_2$) for the 6-azaindole is determined primarily by which protecting group ($PG_1$) is present on the hydroxyl group in the C-3 sidechain, and by consideration of the chemical stability of the amine protecting group ($PG_1$) required in the remaining steps of the synthesis. When the hydroxyl protecting group ($PG_1$) is anO-benzyl ether as illustrated previously in Schemes C and D, the 6-azaindole may be protected as a carbamate derivative such as a tert-butylcarbamate (BOC). In this case, the BOC-protected 6-azaindole is stable under the hydrogenolysis conditions which are used to remove the O-benzyl ether and it may be conveniently removed at the end of the synthesis using acidic conditions. If it is desired to synthesize compounds of formula (I) wherein $R_0$ is alkyl, substituted alkyl or the like, then it is possible to introduce that substituent at this point and the use of a protecting group and its subsequent removal is not required.

An alcohol of general formula 21 may be converted to a primary amine of general formula 23 using a variety of methods known in the literature of organic chemistry. The bottom of Scheme F illustrates a process where the alcohol 21 is first converted to an azide of general formula 22, followed by reduction to afford the amine derivative 23. The synthesis of an azide of general formula 22 from alcohols like 21 is best accomplished by performing a Mitsunobu reaction in the presence of an appropriate azide source such as diphenylphosphoryl azide or zinc azide pyridine complex. Scheme F illustrates the reaction of alcohol 21 with triphenylphosphine, diethylazodicarboxylate, zinc azide pyridine complex and a proton source such as imidazole in an inert solvent like methylene chloride or tetrahydrofuran. The reaction is usually conducted at room temperature for periods between 1–24 hours, typically overnight or about 15 hours, and affords the azide of general formula 22 in good yield. Finally, an azide of formula 22 may then be reduced to an amine of formula 23 using one of several methods common in organic synthesis. One preferred method is catalytic hydrogenation in a solvent like methanol or ethanol in the presence of a catalyst such as 10% palladium on carbon. Alternatively, azides like 22 may be reacted with triphenylphosphine to form an iminophosphorane which upon hydrolysis with water affords the amine of formula 23 and triphenylphophine oxide.

Reaction Scheme G

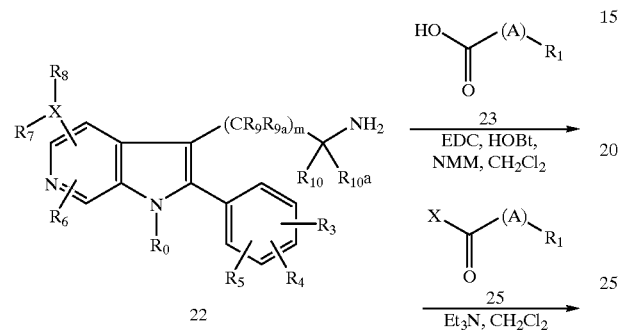

Reaction Scheme H

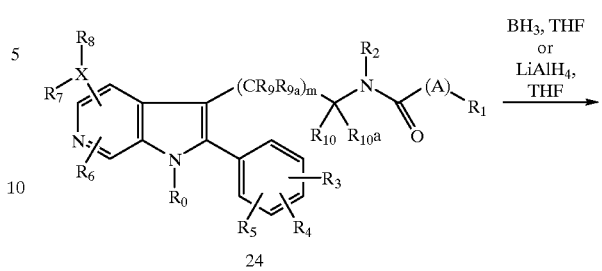

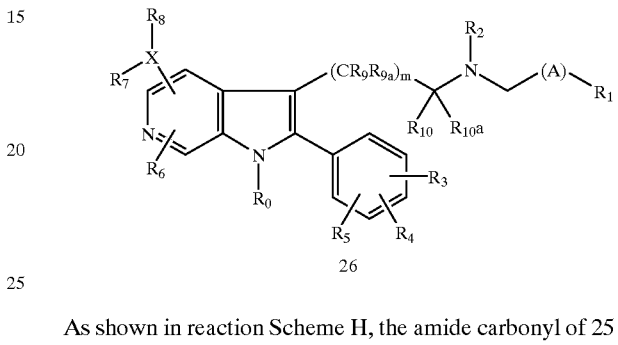

As shown in reaction Scheme H, the amide carbonyl of 25 can be reduced by treatment with borane, lithium aluminum hydride, or equivalent hydride sources in an inert organic solvent such as tetrahydrofuran, diethyl ether, 1,4-dioxane or the like at about 25° C. to about 100° C., preferably about 65° C., for a period of 1–8 hours to give the corresponding amine 27.

Reaction Scheme I

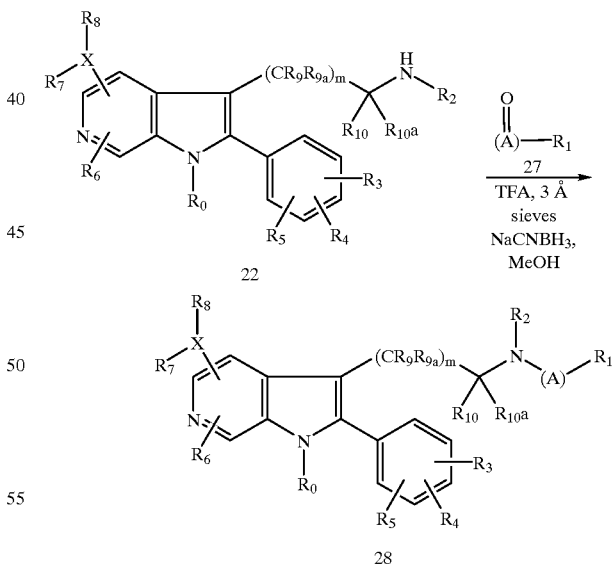

The final stage of the synthesis of the novel 6-azaindole derivatives (I) involves elaboration of the sidechain at the C-3 position of the 6-azaindole core. One method for the completion of the synthesis is illustrated in Scheme G. As shown, the 2-aryltryptamine (23) may be condensed with a carboxylic acid of type 24 using the coupling reagent 1-(3-dimethylamino-propyl)-3-ethylcarbodiimide hydrochloride (EDC), 1,3-dicyclohexyl-carbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours to provide the corresponding amide derivative (25). Alternatively, 2-aryltryptamine 23 can be treated with an active ester or acid chloride of formula 26 in an inert organic solvent such as methylene chloride, chloroform, tetrahydrofuran, diethyl ether, or the like and a tertiary amine base such as triethylamine, diisopropylethylamine, pyridine or the like at a temperature of 0°–25° C. for 30 minutes to 4 hours to give compound 25.

As shown in reaction Scheme I, the 2-aryltryptamine 23 can be modified by treatment with an aldehyde or ketone of type 28 in the presence of a weak acid such as trifluoroacetic acid (TFA), acetic acid or the like, with or without a dessicant such as 3A molecular sieves or magnesium sulfate, and a hydride source such as sodium borohydride or sodium cyanoborohydride, in an inert organic solvent such as methanol, ethanol, isopropanol, tetrahydrofuran, dichloromethane, chloroform, or mixtures thereof at a temperature of about 0° to about 25° C. for a period of 1–12 hours to give the corresponding secondary or tertiary amine derivative 29.

Reaction Scheme J

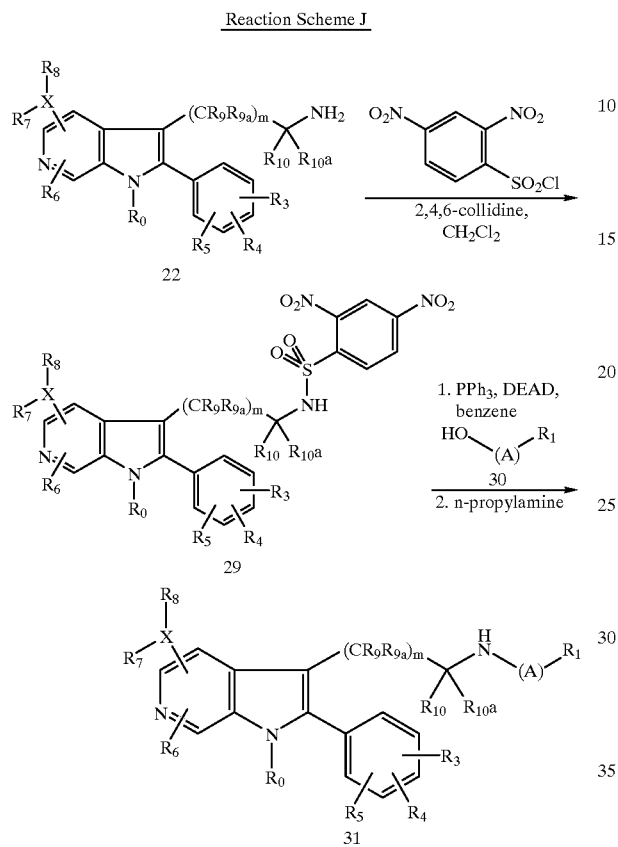

Reaction Scheme K

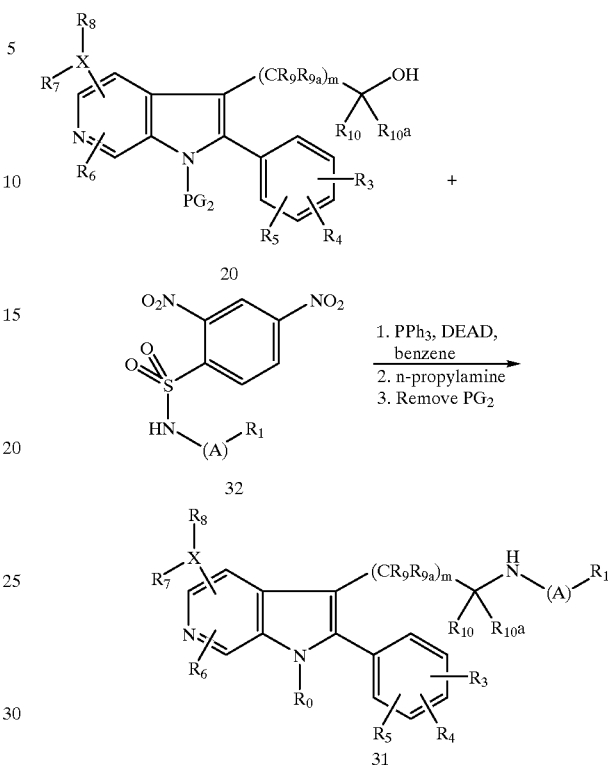

As shown in reaction Scheme J, the tryptamine 23 can be modified using the Fukuyama modification of the Mitsunobu reaction (Fukuyama, T.; Jow, C.-K.; Cheung, M. Tetrahedron Lett. 1995, 36, 6373–74). The tryptamine 23 may be reacted with an arylsufonyl chloride such as 2-nitrobenzene-sulfonyl chloride, 4-nitrobenzenesulfonyl chloride or 2,4-dinitrobenzene-sulfonyl chloride and a hindered amine base such as 2,4,6-collidine, 2,6-lutidine or the like in an inert organic solvent such as methylene chloride to provide the corresponding sulfonamide 30. The sulfonamides can be further modified by reaction with an alcohol of type 31 in the presence of triphenylphosphine and an activating agent such as diethylazodicarboxylate (DEAD), diisopropylazodicaboxylate or the like in an inert organic solvent such as benzene, toluene, tetrahydrofuran or mixtures thereof to give the dialkylsulfonamide adduct. Removal of a dinitrobenzenesulfonyl group is accomplished by treatment with a nucleophilic amine such as n-propylamine or the like in an inert organic solvent such as methylene chloride to give secondary amines of type 32.

When a mono-nitrobenzenesulfonyl derivative is employed, the removal of the sulfonamide is accomplished with a more nucleophilic reagent such as thiophenol or mercaptoacetic acid in combination with lithium hydroxide in DMF.

Reaction Scheme K illustrates a method that is complimentary to reaction Scheme J for completing the synthesis of the novel compounds of formula (I). Scheme K also employs the Fukuyama modification of the Mitsunobu reaction similar to that illustrated in reaction Scheme J. However in this instance, the alcohol partner employed is a 2-aryltryptophol of general formula 21 which has been decribed previously in reaction Scheme F. The 2-aryltryptophol (21) is reacted with a substituted sulfonamide of general formula 33, triphenylphosphine and diethylazodicarboxylate in a suitable inert organic solvent such as benzene, tetrahydrofuran, 1,4-dioxane or the like. The reaction is generally conducted at room temperature for a period of 2 to 24 hours, typically overnight or for about 12–16 hours. The product is an N,N-disubstituted sulfonamide which is then separately subjected to reaction with a base such as n-propylamine which removes the sulfonamide substituent and furnishes a secondary amine related to formula 32. The sulfonamides of formula 33 employed are readily obtained from a primary amine and either 2-nitrobenzenesulfonyl chloride, 4-nitrobenzenesulfonyl chloride or 2,4-dinitrobenzenesulfonyl chloride (as shown) in the presence of a hindered amine base such as 2,4,6-collidine, 2,6-lutidine or the like in an inert organic solvent such as methylene chloride. The final stage of the synthesis requires removal of the protecting group on the 6-azaindole nitrogen atom ($PG_2$) which produces a compound of general formula 32 wherein $R_0$ is a hydrogen atom. It will be recognized by individuals skilled in the art of organic synthesis that a preference for utilizing either the synthetic sequences outlined in reaction Schemes J or K will be determined by the substituents selected to be present in the compounds of formula (I).

The compounds of the present invention are useful in the treatment of various sex-hormone related conditions in men and women. This utility is manifested in their ability to act as antagonists of the neuropeptide hormone GnRH as demonstrated by activity in the following in vitro assays.

Rat pituitary GnRH receptor binding assay:

Crude plasma membranes prepared from rat pituitary tissues were incubated in a Tris.HCL buffer (50 mM, PH. 7.5) containing bovine serum albumin (0.1%), [I-125]D-t-Bu-Ser6-Pro9-ethyl amide-GnRH, and the desired concentration of a test compound. The assay mixtures were incubated at 4° C. for 90–120 minutes followed by rapid filtration and repeated washings through a glass fiber filter. The radioactivity of membrane bound radioligands was determined in a gamma-counter. From this data, the $IC_{50}$ of the radioligand binding to GnRH receptors in the presence of test compound was estimated.

Inhibition of LH release assay:

Active compounds from the GnRH receptor binding assay were further evaluated with an in vitro LH release assay to confirm their antagonist activity (blocking GnRH-induced LH release).

1. Sample Preparation

The compounds to be assayed were dissolved and diluted in DMSO. The final concentration of DMSO in the incubation medium was 0.5%.

2. Assay

The Wistar male rats (150–200 grams) were obtained from Charles River Laboratories (Wilmington, Mass.). Rats were maintained at a constant temperature (25° C.) on a 12-hr light, 12-hr dark cycle. Rat chow and water were available ad libitum. The animals were sacrificed by decapitation and pituitary glands were aseptically removed and placed in Hank's Balanced Salt Solution (HBSS) in a 50-ml polypropylene centriguge tube. The collection tube was centrifuged for 5 min at 250×g, and HBSS was removed by aspiration. Pituitary glands were transferred to a disposable petri plate and minced with a scalpel. The minced tissue was then transferred to a 50-ml disposable centrifuge tube by suspending the tissue fragments in three successive 10-ml aliquots of HBSS containing 0.2% collagenase and 0.2% hyaluronidase. The cell dispersion was carried out in a water bath at 37° C. with gentle stirring for 30 min. At the end of the incubation, the cells were aspirated 20 to 30 times with a pipet and the undigested pituitary fragments were allowed to settle for 3 to 5 min. The suspended cells were removed by aspiration, and then subjected to a 1200 g centrifugation for 5 min. The cells were then resuspended in Culture medium. The undigested pituitary fragments were treated with 30 ml aliquots of the digestion enzymes as above for a total of 3 digestions with the collagenase/hyaluronidase mixture. The resulting cell suspensions were pooled, counted and diluted to a concentration of $3 \times 10^5$ cells/ml, and 1.0 ml of this suspension was placed in each well of a 24-well tray (Costar, Cambridge, Mass.). Cells were maintained in a humidified 5% $CO_2$–95% air atmosphere at 37° C. for 3 to 4 days. The culture medium consisted of DMEM containing 0.37% $NaHCO_3$, 10% horse serum, 2.5% fetal bovine serum, 1% non-essential amino acids, 1% glutamine, and 0.1% gentamycin. On the day of an experiment, cells were washed three times 1½ hrs prior to and two more times immediately before the start of the experiment with DMEM containing 0.37% $NaHCO_3$, 10% horse serum, 2.5% fetal bovine serum, 1% non-essential amino acids(100×), 1% glutamine(100×), 1% Penicillin/Streptomycin(10,000 Units of Penicillin and 10,000 micrograms of Streptomycin per ml), and 25 mM HEPES, pH 7.4. LH release was initiated by adding 1 ml of fresh medium containing test compounds in the presence of 2 nM GnRH to each well in duplicate. Incubation was carried out at 37° C. for 3 hr. After incubation, medium was removed and centrifuged at 2,000×g for 15 min to remove any cellular material. The supernatant fluid was removed and assayed for LH content with a double antibody RIA procedure using materials obtained from Dr. A. F. Parlow (Harbor-UCLA Medical Center, Torrance, Calif.).

The compounds of formula I are useful in a number of areas affected by GnRH. They may be useful in sex-hormone related conditions, sex-hormone dependent cancers, benign prostatic hypertrophy or myoma of the uterus. Sex-hormone dependent cancers which may benefit from the administration of the compounds of this invention include prostatic cancer, uterine cancer, breast cancer and pituitary gonadotrophe adenomas. Other sex-hormone dependent conditions which may benefit from the administration of the compounds of this invention include endometriosis, polycystic ovarian disease, uterine fibroids and precocious puberty. The compounds may also be used in combination with an angiotensin-converting enzyme inhibitor such as Enalapril or Captopril, an angiotensin II-receptor antagonist such as Losartan or a renin inhibitor for the treatment of uterine fibroids.

The compounds of the invention may also be useful for controlling pregnancy, as a contraceptive in both men and women, for in vitro fertilization, in the treatment of premenstrual syndrome, in the treatment of lupus erythematosis, in the treatment of hirsutism, in the treatment of irritable bowel syndrome and for the treatment of sleep disorders such as sleep apnea.

A further use of the compounds of this invention is as an adjunct to growth hormone therapy in growth hormone deficient children. The compounds may be administered with growth hormone or a compound which increases the endogenous production or release of growth hormone. Certain compounds have been developed which stimulate the release of endogenous growth hormone. Peptides which are known to stimulate the release of endogenous growth hormone include growth hormone releasing hormone, the growth hormone releasing peptides GHRP-6 and GHRP-1 (described in U.S. Pat. No. 4,411,890, PCT Patent Pub. No. WO 89/07110, and PCT Patent Pub. No. WO 89/07111) and GHRP-2 (described in PCT Patent Pub. No. WO 93/04081), as well as hexarelin (*J. Endocrinol Invest.*, 15(Suppl 4), 45 (1992)). Other compounds which stimulate the release of endogenous growth hormone are disclosed, for example, in the following: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; EPO Patent Pub. No. 0,144,230; EPO Patent Pub. No. 0,513,974; PCT Patent Pub. No. WO 94/07486; PCT Patent Pub. No. WO 94/08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; *Science* 260, 1640–1643 (Jun. 11, 1993); *Ann. Rep. Med. Chem.*, 28, 177–186 (1993); *Bioorg. Med. Chem. Ltrs.*, 4(22), 2709–2714 (1994); and *Proc. Natl. Acad. Sci. USA* 92, 7001–7005 (July 1995).

Representative preferred growth hormone secretagoues employed in the present combination include the following:

1) N-[1(R)-[(1,2-Dihydro-1-methanesulfonylspiro[3H-indole-3,4'-piperidin]-1'-yl)carbonyl]-2-(1H-indol-3-yl)ethyl]-2-amino-2-methyl-propanamide;
2) N-[1(R)-[(1,2-Dihydro-1-methanecarbonylspiro[3H-indole-3,4'-piperidin]-1'-yl)carbonyl]-2-(1H-indol-3-yl)ethyl]-2-amino-2-methyl-propanamide;
3) N-[1(R)-[(1,2-Dihydro-1-benzenesulfonylspiro[3H-indole-3,4'-piperidin]-1'-yl)carbonyl]-2-(1H-indol-3-yl)ethyl]-2-amino-2-methyl-propanamide;
4) N-[1(R)-[(3,4-Dihydro-spiro[2H-1-benzopyran-2,4'-piperidin]-1'-yl) carbonyl]-2-(1H-indol-3-yl)ethyl]-2-amino-2-methylpropanamide;
5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methyl-propanamide;
6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;
7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide methanesulfonate;
8) N-[1(R)-[(1,2-Dihydro-1-methanesulfonylspiro[3H-indole-3,4'-piperidin]-1'-yl)carbonyl]-2-(2',6'-difluorophenylmethyloxy)ethyl]-2-amino-2-methylpropanamide;
9) N-[1(R)-[(1,2-Dihydro-1-methanesulfonyl-5-fluorospiro[3H-indole-3,4'-piperidin]-1'-yl)carbonyl]-2-(phenylmethyloxy)ethyl] -2-amino-2-methylpropanamide;
10) N-[1(S)-[(1,2-Dihydro-1-methanesulfonylspiro[3H-indole-3,4'-piperidin]-1'-yl) carbonyl]-2-(phenylmethylthio)ethyl]-2-amino-2-methylpropanamide;
11) N-[1(R)-[(1,2-Dihydro-1-methanesulfonylspiro[3H-indole-3,4'-piperidin]-1'-yl)carbonyl]-3-phenylpropyl]-2-amino-2-methyl-propanamide;
12) N-[1(R)-[(1,2-Dihydro-1-methanesulfonylspiro[3H-indole-3,4'-piperidin]-1'-yl)carbonyl]-3-cyclohexylpropyl]-2-amino-2-methyl-propanamide;
13) N-[1(R)-[(1,2-Dihydro-1-methanesulfonylspiro[3H-indole-3,4'-piperidin]-1'-yl)carbonyl]-4-phenylbutyl]-2-amino-2-methyl-propanamide;
14) N-[1(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;
15) N-[1(R)-[(1,2-Dihydro-1-methanesulfonyl-5-fluorospiro[3H-indole-3,4'-piperidin]-1'-yl)carbonyl]-2-(5-fluoro-1H-indol-3-yl)ethyl]-2-amino-2-methylpropanamide;
16) N-[1(R)-[(1,2-Dihydro-1-(2-ethoxycarbonyl) methylsulfonylspiro-[3H-indole-3,4'-piperidin]-1'-yl) carbonyl]-2-(1H-indol-3-yl)ethyl]-2-amino-2-methylpropanamide;
17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide;

and pharmaceutically acceptable salts thereof.

The compounds of the invention may also be used in combination with bisphosphonates (bisphosphonic acids) and other agents, such as growth hormone secretagogues, for the treatment and the prevention of disturbances of calcium, phosphate and bone metabolism, in particular, for the prevention of bone loss during therapy with the GnRH antagonist, and in combination with estrogens, progesterones and or androgens for the prevention or treatment of bone loss or hypogonadal symptoms such as hot flashes during therapy with the GnRH antagonist.

Bisphosphonates (bisphosphonic acids) are known to inhibit bone resorption and are useful for the treatment of bone lithiasis as disclosed in U.S. Pat. No. 4,621,077 to Rosini, et al.

The literature discloses a variety of bisphosphonic acids which are useful in the treatment and prevention of diseases involving bone resorption. Representative examples may be found in the following: U.S. Pat. No. 3,251,907; U.S. Pat. No. 3,422,137; U.S. Pat. No. 3,584,125; U.S. Pat. No. 3,940,436; U.S. Pat. No. 3,944,599; U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,578,376; U.S. Pat. No. 4,621,077; U.S. Pat. No. 4,624,947; U.S. Pat. No. 4,746,654; U.S. Pat. No. 4,761,406; U.S. Pat. No. 4,922,007; U.S. Pat. No. 4,942,157; U.S. Pat. No. 5,227,506; U.S. Pat. No. 5,270,365; EPO Patent Pub. No. 0,252,504; and *J. Org. Chem.*, 36, 3843 (1971).

The preparation of bisphosphonic acids and halobisphosphonic acids is well known in the art. Representative examples may be found in the above mentioned references which disclose the compounds as being useful for the treatment of disturbances of calcium or phosphate metabolism, in particular, as inhibitors of bone resorption.

Preferred bisphosphonates are selected from the group of the following compounds: alendronic acid, etidrononic acid, clodronic acid, pamidronic acid, tiludronic acid, risedronic acid, 6-amino-1-hydroxy-hexylidene-bisphosphonic acid, and 1-hydroxy-3(methylpentylamino)-propylidene-bisphosphonic acid; or any pharmaceutically acceptable salt thereof. A particularly preferred bisphosphonate is alendronic acid (alendronate), or a pharmaceutically acceptable salt thereof. An especially preferred bisphosphonate is alendronate sodium, including alendronate sodium trihydrate. Alendronate sodium has received regulatory approval for marketing in the United States under the trademark FOSAMAX®.

Additionally, a compound of the present invention may be co-administered with a 5α-reductase 2 inhibitor, such as finasteride or episteride; a 5α-reductase 1 inhibitor such as 4,7β-dimethyl-4-aza-5α-cholestan-3-one, 3-oxo-4-aza-4,7β-dimethyl-16β-(4-chlorophenoxy)-5α-androstane, and 3-oxo-4-aza-4,7β-dimethyl-16β-(phenoxy)-5α-androstane as disclosed in WO 93/23420 and WO 95/11254; dual inhibitors of 5α-reductase 1 and 5α-reductase 2 such as 3-oxo-4-aza-17β-(2,5-trifluoromethylphenyl-carbamoyl)-5α-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Further, a compound of the present invention may be used in combination or co-administered with a compound having luteinizing hormone releasing activity such as a peptide or natural hormone or analog thereof. Such peptide compounds include leuprorelin, gonadorelin, buserelin, triptorelin, goserelin, nafarelin, histrelin, deslorelin, meterlin and recirelin.

For combination treatment with more than one active agent, where the active agents are in separate dosage formulations, the active agents may be administered separately or in conjunction. In addition, the administration of one element may be prior to, concurrent to, or subsequent to the administration of the other agent.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethy-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following examples illustrate the preparation of some of the compounds of the invention and are not to be construed as limiting the invention disclosed herein.

EXAMPLE 1

Following procedures similar to those described in Schemes A to K, the following compounds are prepared:

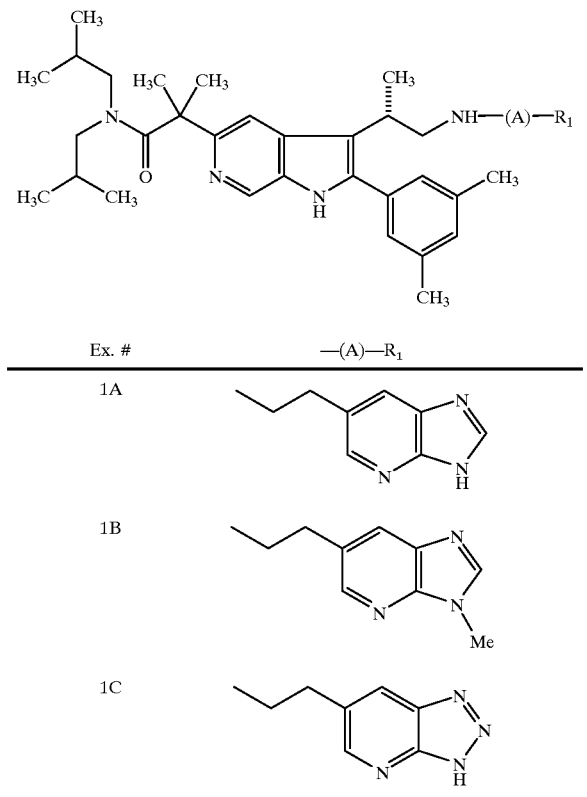

What is claimed is:

1. A compound of the formula

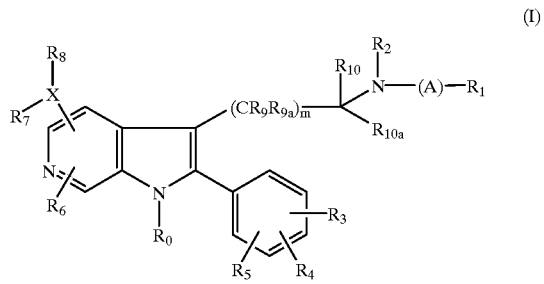

wherein

A is $C_1$–$C_6$ alkyl, substituted $C_1$–$C_6$ alkyl, $C_3$–$C_7$ cycloalkyl, substituted $C_3$–$C_7$ cycloalkyl, $C_3$–$C_6$ alkenyl, substituted $C_3$–$C_6$ alkenyl, $C_3$–$C_6$ alkynyl, substituted $C_3$–$C_6$ alkynyl, $C_1$–$C_6$ alkoxy, or $C_0$–$C_5$ alkyl-S(O)$_n$—$C_0$–$C_5$ alkyl, $C_0$–$C_5$ alkyl-O-$C_0$–$C_5$ alkyl, $C_0$–$C_5$ alkyl-NR$_{18}$—$C_0$–$C_5$ alkyl where $R_{18}$ and the $C_0$–$C_5$ alkyl can be joined to form a ring, or a single bond.

$R_0$ is hydrogen, $C_1$–$C_6$ alkyl, substituted $C_1$–$C_6$ alkyl, wherein the substituents are as defined below; aryl, substituted aryl, aralkyl or substituted aralkyl, wherein the substituents are as defined for $R_3$, $R_4$ and $R^5$ $R_1$ is
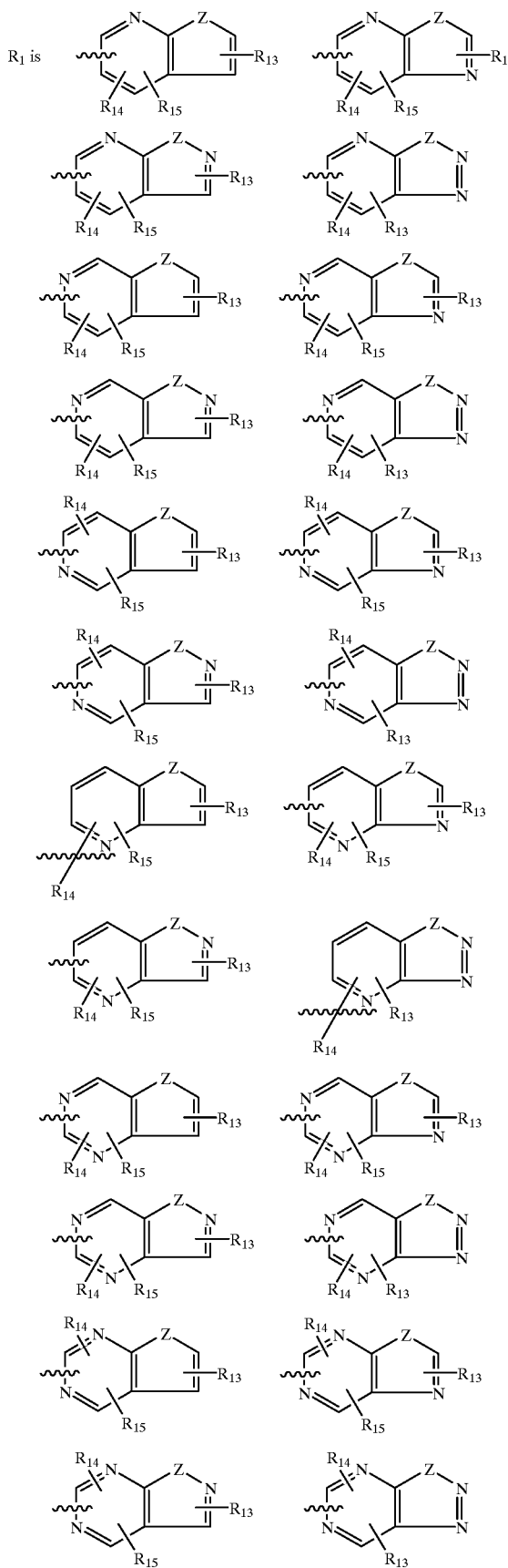
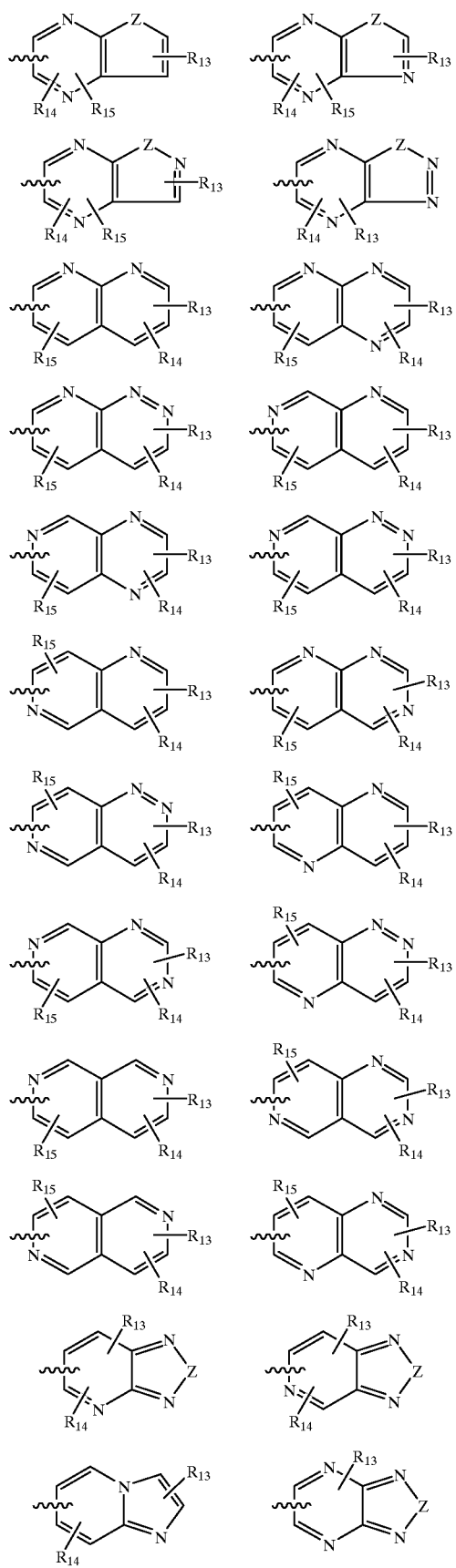

-continued

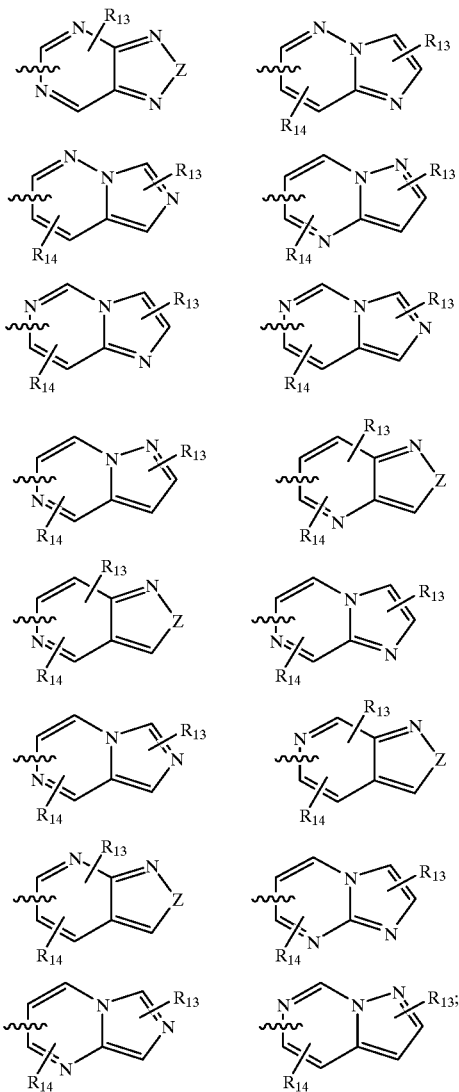

the nitrogen atoms contained in the $R_1$ heteroaromatic rings may exist either as drawn or, when chemically allowed, in their oxidized (N→O) state;

$R_2$ is hydrogen, $C_1$–$C_6$ alkyl, substituted $C_1$–$C_6$ alkyl, aralkyl, substituted aralkyl, aryl, substituted aryl, alkyl —$OR_{11}$, $C_1$–$C_6(NR_{11}R_{12})$, $C_1$–$C_6(CONR_{11}R_{12})$ or $C(NR_{11}R_{12})NH$;

$R_2$ and A taken together form a ring of 5–7 atoms;

$R_3$, $R_4$ and $R_5$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_3$ and $R_4$ taken together form a carbocyclic ring of 3–7 carbon atoms or a heterocyclic ring containing 1–3 heteroatoms selected from N, O and S;

$R_6$ is hydrogen, $C_1$–$C_6$ alkyl, substituted $C_1$–$C_6$ alkyl, aryl, substituted aryl, $C_1$–$C_3$ perfluoroalkyl, CN, $NO_2$, halogen, $R_{11}O(CH_2)_p$—, $NR_{12}C(O)R_{11}$, $NR_{12}C(O)NR_{11}R_{12}$ or $SO_nR_{11}$;

$R_7$ is hydrogen, $C_1$–$C_6$ alkyl, or substituted $C_1$–$C_6$ alkyl, unless X is hydrogen or halogen, then $R_7$ is absent;

$R_8$ is hydrogen, $C(O)OR_9$, $C(O)NR_{11}R_{12}$, $NR_{11}R_{12}$, $C(O)R_{11}$, $NR_{12}C(O)R_{11}$, $NR_{12}C(O)NR_{11}R_{12}$, $NR_{12}S(O)_2R_{11}$, $NR_{12}S(O)_2NR_{11}R_{12}$, $OC(O)R_{11}$, $OC(O)NR_{11}R_{12}$, $OR_{11}$, $SO_nR_{11}$, $S(O)_nNR_{11}R_{12}$, $C_1$–$C_6$ alkyl or substituted $C_1$–$C_6$ alkyl, unless X is hydrogen or halogen, then $R_8$ is absent; or $R_7$ and $R_8$ taken together form a carbocyclic ring of 3–7 atoms;

$R_9$ and $R_{9a}$ are independently hydrogen, $C_1$–$C_6$ alkyl, substituted $C_1$–$C_6$ alkyl; aryl or substituted aryl, aralkyl or substituted aralkyl when m≠0; or $R_9$ and $R_{9a}$ taken together form a carbocyclic ring of 3–7 atoms or

when m≠0;

$R_9$ and A taken together form a heterocyclic ring containing 3–7 carbon atoms and one or more heteroatoms when m≠0; or $R_{10}$ and $R_{10a}$ are independently hydrogen, $C_1$–$C_6$ alkyl, substituted $C_1$–$C_6$ alkyl, aryl, substituted aryl, aralkyl or substituted aralkyl; or $R_{10}$ and $R_{10a}$ taken together form a carbocyclic ring of 3–7 atoms or

$R_9$ and $R_{10}$ taken together form a carbocyclic ring of 3–7 carbon atoms or a heterocyclic ring containing one or more heteroatoms when m≠0; or $R_9$ and $R_2$ taken together form a heterocyclic ring containing 3–7 carbon atoms and one or more heteroatoms when m≠0; or $R_{10}$ and $R_2$ taken together form a heterocyclic ring containing 3–7 carbon atoms and one or more heteroatoms;

$R_{10}$ and A taken together form a heterocyclic ring containing 3–7 carbon atoms and one or more heteroatoms; or $R_{11}$ and $R_{12}$ are independently hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

$R_{11}$ and $R_{12}$ taken together can form an optionally substituted ring of 3–7 atoms;

$R_{13}$ is hydrogen, OH, $NR_7R_8$, $NR_{11}SO_2(C_1$–$C_6$ alkyl), $NR_{11}SO_2$(substituted $C_1$–$C_6$ alkyl), $NR_{11}SO_2$(aryl), $NR_{11}SO_2$(substituted aryl), $NR_{11}SO_2(C_1$–$C_3$ perfluoroalkyl); $SO_2NR_{11}(C_1$–$C_6$ alkyl), $SO_2NR_{11}$(substituted $C_1$–$C_6$ alkyl), $SO_2NR_{11}$(aryl), $SO_2NR_{11}$(substituted aryl), $SO_2NR_{11}(C_1$–$C_3$ perfluoroalkyl); $SO_2NR_{11}(C(O)C_1$–$C_6$ alkyl); $SO_2NR_{11}(C(O)$-substituted $C_1$–$C_6$ alkyl); $SO_2NR_{11}(C(O)$-aryl); $SO_2NR_{11}(C(O)$-substituted aryl); $S(O)_n(C_1$–$C_6$ alkyl); $S(O)_n$(substituted $C_1$–$C_6$ alkyl), $S(O)_n$(aryl), $S(O)_n$(substituted aryl), $C_1$–$C_3$ perfluoroalkyl, $C_1$–$C_3$ perfluoroalkoxy, $C_1$–$C_6$ alkoxy, substituted $C_1$–$C_6$ alkoxy, COOH, halogen, $NO_2$ or CN;

$R_{14}$ and $R_{15}$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, $R_{11}C(O)O(CH_2)_p$—, $R_{11}OC(O)(CH_2)_p$—, —$(CH_2)_pS(O)_nR_{17}$, —$(CH_2)_pC(O)NR_{11}R_{12}$ or halogen; wherein $R_{17}$ is hydrogen, $C_1$–$C_6$ alkyl, $C_1$–$C_3$ perfluoroalkyl, aryl or substituted aryl;

$R_{18}$ is hydrogen, $C_1$–$C_6$ alkyl, substituted $C_1$–$C_6$ alkyl, $C(O)OR_9$, $C(O)NR_{11}R_{12}$, $C(O)R_{11}$, $S(O)_nR_{11}$;

$R_{19}$ is either the definition of $R_{13}$ or $R_{14}$;

X is hydrogen, halogen, N, O, $S(O)_n$, $C(O)$, $(CR_{11}R_{12})_p$; $C_2$–$C_6$ alkenyl, substituted $C_2$–$C_6$ alkenyl,$C_2$–$C_6$ alkynyl, or substituted $C_2$–$C_6$ alkynyl; when X is hydrogen or halogen, $R_7$ and $R_8$ are absent; when X is O, $S(O)_n$, $C(O)$, or $CR_{11}R_{12}$ only $R_7$ or $R_8$ is possible.

Z is O, S, or $NR_{11}$;

m is 0–3;

n is 0–2;

p is 0–4; and the alkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, $C(O)OR_{11}$, aryl $C_1$–$C_3$ alkoxy, substituted aryl $C_1$–$C_3$ alkoxy, and the aryl substituents are as defined for $R_3$, $R_4$ and $R_5$;

or a pharmaceutically acceptable addition salt and/or hydrate thereof, or where applicable, a geometric or optical isomer or racemic mixture thereof.

2. The compound according to claim 1 of the formula

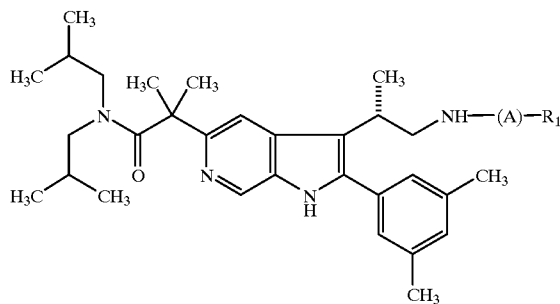

or a pharmaceutically acceptable addition salt and/or hydrate thereof, or where applicable, a geometric or optical isomer or racemic mixture thereof, wherein A and $R_1$ are as indicated in the following table:

| Ex. # | —(A)—$R_1$ |
|---|---|
| 1A | (propyl-imidazo[4,5-b]pyridine, NH) |
| 1B | (propyl-imidazo[4,5-b]pyridine, N-Me) |
| 1C | (propyl-triazolo[4,5-b]pyridine, NH) |

3. A pharmaceutical composition which comprises an effective amount of a compound as defined in claim 1 and a pharmaceutically acceptable carrier therefor.

4. A method for antagonizing gonadotropin-releasing hormone in a subject in need thereof which comprises administering to said subject an effective amount of a compound as defined in claim 1 to a subject suffering from a gonadotropin-releasing hormone derived disorder.

5. A method according to claim 4 wherein the gonadotropin-releasing hormone derived disorder is a sex-hormone related condition.

6. A method according to claim 4 wherein the gonadotropin-releasing hormone derived disorder is a sex hormone dependent cancer, benign prostatic hypertropy or myoma of the uterus.

7. A method according to claim 6 wherein the sex hormone dependent cancer is selected from the group consisting of prostatic cancer, uterine cancer, breast cancer and pituitary gonadotrophe adenomas.

8. A method according to claim 5 wherein the sex hormone related condition is selected from the group consisting of endometriosis, polycystic ovarian disease, uterine fibroids and precocious puberty.

9. A method for preventing pregnancy in a subject in need thereof which comprises administering an effective amount of a compound as defined in claim 1.

10. A method for treating lupus erythematosis in a subject in need thereof which comprises administering to said subject an effective amount of a compound as defined in claim 1.

11. A method for treating irritable bowel syndrome in a subject in need thereof which comprises administering to said subject an effective amount of a compound as defined in claim 1.

12. A method for treating premenstrual syndrome in a subject in need thereof which comprises administering to said subject an effective amount of a compound as defined in claim 1.

13. A method for treating hirsutism in a subject in need thereof which comprises administering to said subject an effective amount of a compound as defined in claim 1.

14. A method for treating short stature or a growth hormone deficiency in a subject in need thereof which comprises administering to said subject an effective amount of a compound which stimulates the endogenous production or release of growth hormone and an effective amount of a compound as defined in claim 1.

15. A method for treating sleep disorders in a subject in need thereof which comprises administering to said subject an effective amount of a compound as defined in claim 1.

16. The method of claim 15 wherein the sleep disorder is sleep apnea.

17. A pharmaceutical composition made by combining the compound of claim 1 and a pharmaceutically acceptable carrier therefor.

18. A process for making a pharmaceutical composition comprising combining a compound of claim 1 and a pharmaceutically acceptable carrier.

* * * * *